(12) United States Patent
Wen

(10) Patent No.: US 9,226,769 B2
(45) Date of Patent: Jan. 5, 2016

(54) RAILWAY LUMBAR COMBINED PUNCTURING NEEDLE

(76) Inventor: Yihui Wen, Zhejiang Province (CN)

(*) Notice: Subject to any disclaimer, the term of this patent is extended or adjusted under 35 U.S.C. 154(b) by 595 days.

(21) Appl. No.: 12/300,167

(22) PCT Filed: May 11, 2007

(86) PCT No.: PCT/CN2007/001541
§ 371 (c)(1),
(2), (4) Date: Nov. 10, 2008

(87) PCT Pub. No.: WO2007/131442
PCT Pub. Date: Nov. 22, 2007

(65) Prior Publication Data
US 2009/0240205 A1  Sep. 24, 2009

(30) Foreign Application Priority Data

May 12, 2006  (CN) ...................... 2006 2 0115262 U

(51) Int. Cl.
*A61M 5/178* (2006.01)
*A61B 17/34* (2006.01)

(52) U.S. Cl.
CPC .................................. *A61B 17/3401* (2013.01)

(58) Field of Classification Search
CPC ........... A61B 17/3401; A61B 17/3415; A61B 17/3417; A61B 2017/3456; A61B 17/3496; A61B 17/3474; A61M 19/00; A61M 25/065; A61M 25/0662; A61M 25/0102; A61M 2005/1587; A61M 2025/0007; A61M 2025/0004

USPC ................. 604/272–274, 161, 173, 158, 160
See application file for complete search history.

(56) References Cited

U.S. PATENT DOCUMENTS

| 4,354,491 A * | 10/1982 | Marbry ......................... 604/160 |
| 4,808,157 A * | 2/1989 | Coombs ......................... 604/44 |
| 5,213,578 A * | 5/1993 | Heiliger et al. ................ 604/158 |
| 5,478,328 A * | 12/1995 | Silverman et al. ............ 604/272 |
| 6,004,293 A * | 12/1999 | Bell .............................. 604/160 |
| 2005/0203465 A1 | 9/2005 | Llurba |

FOREIGN PATENT DOCUMENTS

| CN | 2103319 U | 5/1992 |
| CN | 2380189 Y | 5/2000 |
| CN | 2618569 Y | 6/2004 |

\* cited by examiner

*Primary Examiner* — Kami A Bosworth
*Assistant Examiner* — Bradley G Thomas, Jr.
(74) *Attorney, Agent, or Firm* — Rabin & Berdo, P.C.

(57) ABSTRACT

The present invention provides a puncture needle set for combined spinal-epidural anesthesia comprising an epidural needle with a small guiding conduit on the pin and a groove on the outer wall and a spinal needle with a beaked tip. During anesthesia, first the epidural needle is punctured into the epidural space, then the epidural catheter is placed, afterwards the spinal needle is guided to enter into the groove on the needle peduncle by the small conduit on the pin of the epidural needle and slide into the epidural space, then let it go ahead deep into subarachnoid space. After medicine is injected, the spinal needle and the epidural needle are withdrawn in turn, at the same time the epidural catheter is left back.

2 Claims, 3 Drawing Sheets

RAILWAY LUMBAR COMBINED PUNCTURING NEEDLE

FIELD OF THE INVENTION

The present invention relates to a rail guided puncture needle for combined spinal-epidural anesthesia.

BACKGROUND OF THE INVENTION

According to conventional puncture technique, the anesthesia puncture process is started with the epidural needle punctures into the epidural space, then the spinal needle is delivered into the epidural space through the inner cavity of the epidural needle and further pierced the spine dura mater and the arachnoid mater arriving at the subarachnoid space. After medicine is injected, the spinal needle is withdrawn. The epidural needle is withdrawn after the epidural catheter is placed through the epidural needle to complete the anesthesia puncture process.

SUMMARY OF THE INVENTION

The objective of the invention is to overcome the shortcomings of prior art and provide a practical, scientific and rational combined lumber puncture needle. A combined railway lumbar puncture needle is provided, which comprises epidural needle (1) and spinal needle (2), wherein a small guiding conduit (3) is disposed on the pin (11) of the epidural needle, a groove (8) is provided on the outer wall of the needle peduncle (10) as railway, and the tip of the spinal needle is beaked (4) and is of a unilaterally curved configuration. As illustrated in FIGS. 1 and 4, the epidural needle 1 has an inner cavity through which an epidural catheter is placeable. The inner cavity has two sections. One section of the inner cavity is formed in the pin, and the other section of the inner cavity is formed in the needle peduncle. The groove is separate from the section of the inner cavity formed in the needle peduncle by the outer wall of the needle peduncle.

Compared to prior art, the present invention has advantages as below:
1. The present invention enables the epidural catheter to be placed before medicine is injected into the subarachnoid space, thus avoids the awkwardness of the difficulty in placing catheter into epidural space after medicine is injected into the subarachnoid space.
2. The present invention avoids the possibility of the epidural catheter's accidental entering the subarachnoid space through the spinal needle by the eyelet left on the spinal dura mater.
3. The present invention properly alters the angle between the plane of the outlet of tip of the epidural needle and the vertical axis of the needle peduncle, thus facilitates the epidural catheter to be leaded into the epidural space.

DETAILED DESCRIPTION OF THE INVENTION

Figure 1:
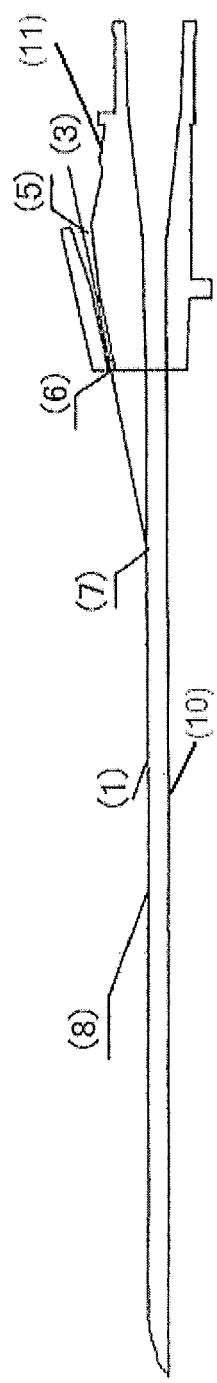
FIG. 1 is a two-dimensional cross-sectional illustration.
Figure 2:
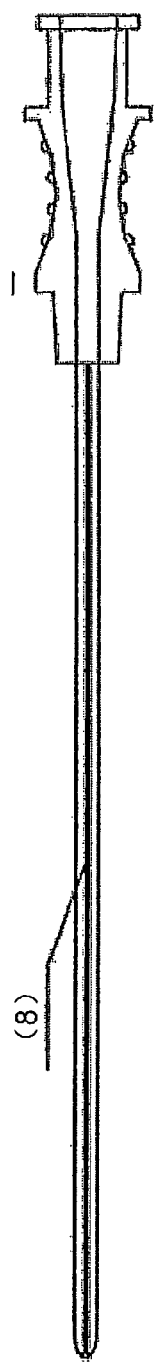
FIG. 2 is a partial cross-sectional view, of the epidural needle, wherein (5) shows the inlet of the conduit (3), (6) shows the outlet of the conduit (3), disposed above the groove (8), and (7) shows the crosslink of the extended line of the conduit (3) and the groove (8) on the needle peduncle, with an oblique angle formed therebetween, as illustrated in FIG. 2.
Figure 3:
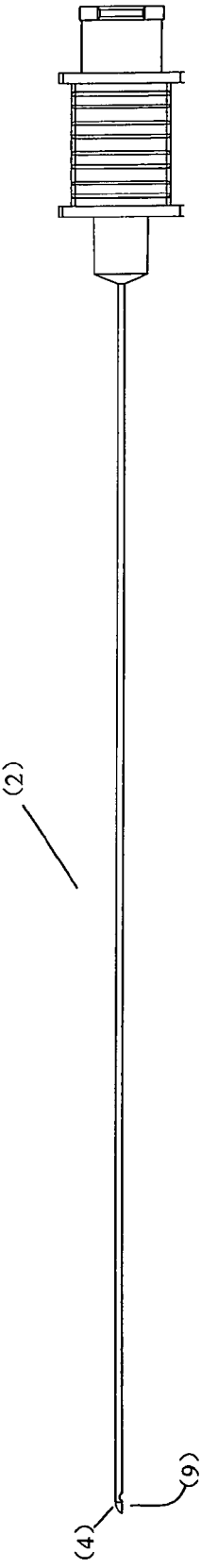
FIG. 3 is the two-dimensional cross-sectional illustrations of spinal needle, wherein (4) shows the beaked tip of the spinal needle.
Figure 4:
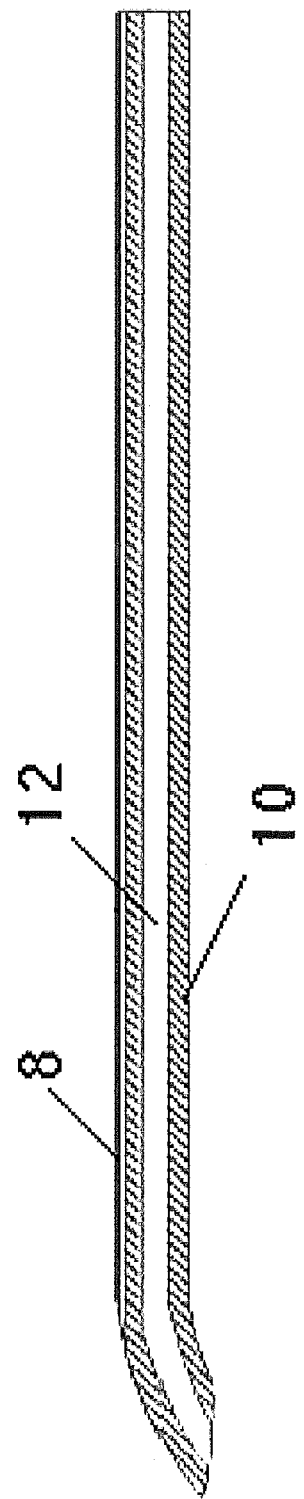
FIG. 4 is a cross-sectional view of the needle peduncle of the epidural needle.

The railway lumber combined puncture needle is used as follows: first, as used in a conventional puncture technique, an epidural needle (1) is first punctured into the epidural space, and an epidural catheter is placed through the epidural needle. Then, a spinal needle (2), with its tip (4) pointing forward, is inserted into the small conduit (3) on the pin of the epidural needle (1) via the inlet (5) thereof. The spinal needle (2) is then pushed forward to exit the outlet (6), until its tip (4) intersect with the groove (8) (i.e. the railway) on the peduncle of the epidural needle at (7). The spinal needle (2) is pushed forward further to make it go along the groove (8) to slide into the epidural space, the ventral side (9) of the beaked tip (4) of the spinal needle slide clinging to the bottom of the railway to avoid the spinal needle's departing from the railway. Pushed ahead somewhat, the core of the spinal needle is withdrawn when feel empty. When the cerebral spinal fluid is seen going out, which approves the tip is in the subarachnoid space, local anesthetics is injected by the needle into the subarachnoid space, then the spinal needle is withdrawn. Afterwards the epidural needle is withdrawn, and the epidural catheter is left to complete the puncture process.

The invention claimed is:

1. A single-lumen combined railway lumbar puncture needle, comprising:
   an epidural needle having an inner cavity through which an epidural catheter is placeable, the epidural needle having a pin and a needle peduncle, the inner cavity having two sections, one section being formed in the pin and the other section being formed in the needle peduncle, a guiding conduit being disposed on the pin of the epidural needle, and a groove being formed on an outer wall of the entire needle peduncle, the groove being separate from the section of the inner cavity formed in the needle peduncle by the outer wall of the needle peduncle, and
   a spinal needle, a tip of the spinal needle being beaked and being of a unilaterally curved configuration, the spinal needle being insertable into the groove via the guiding conduit, and being slidable along the groove, so as to be deliverable through the groove on the epidural needle while the epidural catheter is disposed in place through the inner cavity of the epidural needle, to thereby achieve spinal-epidural anesthesia,
   wherein the inner cavity extends along the epidural needle and is enclosed by the outer wall of the epidural needle, two openings of the inner cavity being respectively formed at approximately two ends of the epidural needle.

2. A combined railway lumbar puncture needle, comprising:
   an epidural needle having an inner cavity through which an epidural catheter is placeable, the epidural needle having a pin that has a guiding conduit, and a needle peduncle extending from the pin, the inner cavity having two sections, one section being formed in the pin and the other section being formed in the needle peduncle, the guiding conduit being separate from the section of the inner cavity formed in the pin, said needle peduncle having a groove formed in an entire outer wall thereof, the groove being separate from the section of the inner cavity formed in the needle peduncle by the outer wall of the needle peduncle, the groove extending an entire length of said needle peduncle and being coplanar with the guiding conduit and forming an oblique angle with an extended line of the guiding conduit, an outlet of the guiding conduit being disposed above the groove; and a spinal needle, a tip of the spinal needle being beaked and being of a unilaterally curved configuration, the spinal needle being insertable into the groove via the guiding conduit, and being slidable along the groove, the beaked tip of the spinal needle being received and guided by the groove;

wherein when said spinal needle is inserted into said guiding conduit, said spinal needle is initially guided in a direction that is oblique to the groove so that the beaked tip, after it passes from the outlet of the guiding conduit, passes above the groove without contacting groove, and subsequently makes contact with and enters the groove at an intermediate portion thereof, to thereafter be guided by the groove, so as to be deliverable through the groove on the epidural needle while the epidural catheter is disposed in place through the inner cavity of the epidural needle, to thereby achieve spinal-epidural anesthesia, and wherein the inner cavity extends along the epidural needle and is enclosed by the outer wall of the epidural needle, two openings of the inner cavity being respectively formed at approximately two ends of the epidural needle.

\* \* \* \* \*